(12) United States Patent
Beike et al.

(10) Patent No.: US 11,549,939 B2
(45) Date of Patent: Jan. 10, 2023

(54) METHOD FOR DETECTING AND/OR CHARACTERIZING THE INTERACTION BETWEEN PROTEINS AND SMALL MOLECULES

(71) Applicant: Dynamic Biosensors GmbH, Martinsried/Planegg (DE)

(72) Inventors: Hanna Beike, Munich (DE); Herwin Daub, Munich (DE); Ismajli Fjolla, Munich (DE); Andreas Langer, Munich (DE); Ulrich Rant, Munich (DE); Ralf Strasser, Munich (DE)

(73) Assignee: DYNAMIC BIOSENSORS GMBH, Munich (DE)

( * ) Notice: Subject to any disclaimer, the term of this patent is extended or adjusted under 35 U.S.C. 154(b) by 438 days.

(21) Appl. No.: 16/624,793

(22) PCT Filed: Jun. 21, 2018

(86) PCT No.: PCT/EP2018/066618
§ 371 (c)(1),
(2) Date: Dec. 19, 2019

(87) PCT Pub. No.: WO2018/234473
PCT Pub. Date: Dec. 27, 2018

(65) Prior Publication Data
US 2020/0132678 A1     Apr. 30, 2020

(30) Foreign Application Priority Data

Jun. 21, 2017 (EP) .................................. 17177037

(51) Int. Cl.
*G01N 33/542* (2006.01)
*G01N 21/64* (2006.01)
*C12Q 1/6825* (2018.01)
*C12Q 1/6834* (2018.01)

(52) U.S. Cl.
CPC ......... *G01N 33/542* (2013.01); *C12Q 1/6825* (2013.01); *C12Q 1/6834* (2013.01); *G01N 21/6428* (2013.01)

(58) Field of Classification Search
None
See application file for complete search history.

(56) References Cited

U.S. PATENT DOCUMENTS

| 2008/0044826 A1* | 2/2008 | Heyduk | G01N 33/542 435/6.12 |
| 2008/0171322 A1 | 7/2008 | Heyduk et al. | |
| 2013/0323726 A1* | 12/2013 | Shekdar | C12Q 1/6809 435/6.11 |

FOREIGN PATENT DOCUMENTS

WO    WO 2017/055463 A1    4/2017

OTHER PUBLICATIONS

Cléry et al., "switchSENSE: A new technology to study protein-RNA interactions," *Methods*, 118-119: 137-145 (Mar. 9, 2017).
(Continued)

*Primary Examiner* — Robert T. Crow
(74) *Attorney, Agent, or Firm* — Leydig, Voit & Mayer, Ltd.

(57) ABSTRACT

A method for characterizing the interaction between a protein and a small molecule by detecting a change in fluorescence emitted by a fluorescent dye and a nucleic acid structure which can be used in said method.

3 Claims, 11 Drawing Sheets

(56) References Cited

OTHER PUBLICATIONS

Fujiwara et al., "Sandwich enzyme immunoassay of tumor-associated antigen sialosylated Lewis$^x$ using β-d-galactosidase coupled to a monoclonal antibody of IgM isotype," *J. of Immunological Methods*, 112(1): 77-83 (Mar. 15, 1988).
Hegner et al., "Immobilizing DNA on gold via thiol modification for atomic force microscopy imaging in buffer solutions," *FEBS Letters*, 336(3): 452-456 (Dec. 1993).
Knezevic et al., "Quantitation of affinity, avidity, and binding kinetics of protein analytes with a dynamically switchable biosurface," *J. of the Amer. Chem. Soc.*, 134: 15225-15228 (2012).
Karaman et al., "A quantitative analysis of kinase inhibitor selectivity," *Nature Biotechnology*, 26(1): 127-132 (Jan. 2008).
Langer et al., "Protein analysis by time-resolved measurements with an electro-switchable DNA chip," *Nature Communications*, 4(2099): 1-8 (Jul. 10, 2013).
Peeters et al., "Comparison of four bifunctional reagents for coupling peptides to proteins and the effect of the three moieties on the immunogenicity of the conjugates," *J. of Immunological Methods*, 120(1): 133-143 (Jan. 17, 1989).
Stephanopoulos et al., "Choosing an effective protein bioconjugation strategy," *Nature Chemical Biology*, 7(12): 876-884 (Nov. 15, 2011).
European Patent Office, International Search Report in International Patent Application No. PCT/EP2018/066618, 4 pp. (dated Sep. 18, 2018).
European Patent Office, Written Opinion in International Patent Application No. PCT/EP2018/066618, 5 pp. (dated Sep. 18, 2018).

* cited by examiner

US 11,549,939 B2

METHOD FOR DETECTING AND/OR CHARACTERIZING THE INTERACTION BETWEEN PROTEINS AND SMALL MOLECULES

CROSS-REFERENCE TO RELATED APPLICATIONS

This application is the U.S. national phase of International Patent Application PCT/EP2018/066618, filed Jun. 21, 2018, which claims the benefit of European Patent Application 17177037.3, filed Jun. 21, 2017, both of which are hereby incorporated by reference in their entireties herein.

FIELD OF THE INVENTION

The present invention relates to a method for detecting and/or characterizing the interaction between a protein and a small molecule by detecting a change in fluorescence emitted by a fluorescent dye and to a nucleic acid structure which can be used in said method.

BACKGROUND OF THE INVENTION

Small molecules can interact with a protein and affect its activity. Therefore, the identification of small molecules which affect the activity of proteins which are involved in pathological processes such as the development of cancer has gained much interest.

For the development of small molecule protein binders it is necessary to characterize their interaction with the target protein. Accurate and precise kinetic measurements for determination of the rate constants $k_{on}$, $k_{off}$ as well as dissociation constant Kd provide information about the binding properties of the small molecule. The $K_d$ may affect the efficacy of the small molecule and influence the pharmacokinetics and dosing strategy.

Several assays for characterizing the interaction between proteins and small molecules have been described in the literature and are also commercially available. One example of such an assay is the LanthaScreen Eu Kinase binding assay available from ThermoFisher which relies on the competitive binding of a fluorescence-labelled compound to a kinase which can be detected by FRET (Förster resonance energy transfer) using a labelled antibody against the tagged kinase.

Nevertheless, there is still a need for methods which enable the exact characterization of the interaction between a protein and a small molecule.

SUMMARY OF THE INVENTION

The object of the present invention is solved by the subject-matter of the independent claims. Further embodiments and advantages of the invention are incorporated in the dependent claims.

The present inventors provide a method which enables to continuously monitor the association and dissociation of a small molecule with a protein so that a time course of association and dissociation can be provided. This enables the exact characterization of the interaction between the small molecule and the protein. The method of the present invention can be used in the high throughput screening of small molecules as protein effectors.

Accordingly, the present invention relates to a method for detecting and/or characterizing the interaction between a protein and a small molecule, comprising the steps of:

a) providing a solid surface to which at least one linker is bound, wherein the protein, at least one fluorescent dye and a competitor compound are attached to the at least one linker and wherein the competitor compound binds to the protein;

b) contacting the solid surface with the small molecule under conditions that allow the small molecule to bind to the protein and to release the competitor compound from the protein; and c) detecting a change in the fluoresence emitted by the fluorescent dye.

In one embodiment, the protein is attached to a first linker and one fluorescent dye and the competitor compound are attached to a second linker.

In another embodiment, the protein, one fluorescent dye and the competitor compound are all attached to the same linker. This linker may have two branches, wherein the protein and one fluorescent dye are attached to the first branch and the competitor compound is attached to the second branch.

In one embodiment, the solid surface is a metal surface.

The linker may be a nucleic acid linker which may be double-stranded.

By detecting the change in fluorescence emitted by the fluorescent dye the time course of association and/or dissociation of the small molecule with the protein may be measured.

In one embodiment the change in fluorescence is detected continuously after the solid surface has been contacted with the small molecule.

In one embodiment, the competitor compound is able to quench the fluorescence of the fluorescent dye, for example after the competitor compound has been released from the protein.

In one embodiment a quencher is attached to the linker.

The present invention is also directed to a nucleic acid structure comprising:

(i) a first and a second nucleic acid molecule which form a double strand with each other over a part of the first and a part of the second nucleic acid molecule;

(ii) a third nucleic acid molecule which forms a double strand with a part of the first nucleic acid molecule which does not form a double strand with the second nucleic acid molecule; and (iii) a fourth nucleic acid molecule which forms a double strand with a part of the second nucleic acid molecule which does not form a double strand with the first nucleic acid molecule, wherein:

a fluorescent dye is attached to the first nucleic acid molecule;

a quencher is attached to the second nucleic acid molecule;

a protein is attached to the third nucleic acid molecule, and a competitor compound is attached to the fourth nucleic acid molecule.

This nucleic acid structure can be used for characterizing the interaction between a protein and a small molecule.

The present invention also relates to a solid surface to which one or more of said nucleic acid structures are attached.

Figure 1:
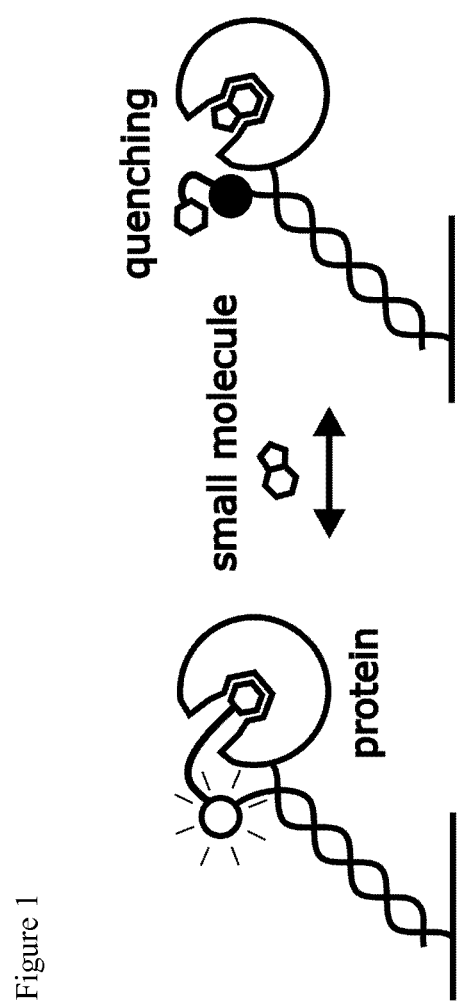
FIG. 1: Interaction between competitor compound (shown as hexagon) and protein (shown as circle with an opening) wherein the protein, the competitor compound and the fluorescent dye (shown as circle surrounded by rays) are all attached to the same DNA double strand.

On the left part the competitor compound binds to a binding site within the protein and the fluorescent dye emits fluorescence. When the solid surface is contacted with the small molecule, the competitor compound is released, leading to quenching of the fluorescence emitted by the fluorescent dye which is therefore shown as a black circle (see right part).

FIG. 2: Interaction between competitor compound (shown as hexagon) and protein (shown as circle with an opening) wherein the protein is bound to a first DNA double strand and the competitor compound is bound to a second DNA double strand. To both the first and the second DNA double strand a fluorescent dye (shown as circle or star surrounded by rays) is attached.

a) In this example the first and the second DNA double strand consist of single strands with the same sequence. Two identical fluorescent dyes (shown as circles) are attached to the first and the second DNA double strand.

On the left part the competitor compound binds to a binding site within the protein and the fluorescent dye emits fluorescence. When the solid surface is contacted with the small molecule, the competitor compound is released, leading to quenching of the fluorescence emitted by the fluorescent dye which is therefore shown as a black circle (see right part).

b) This figure shows the association (left) and dissociation (right) of the small molecule SB203580 with the protein p38 kinase using the competitor compound PP58 and a Cy3-like fluorescent dye, wherein the protein and the fluorescent dye are attached to a first DNA double strand and the competitor compound is attached to a second DNA double strand. The fluorescence decreases upon binding of the small molecule due to the quenching by the competitor compound.

c) In this example the first and the second DNA double strand do not consist of single strands with the same sequence. Accordingly, the first DNA double strand is shown as solid line and the second DNA double strand is shown as dashed line. The first fluorescent dye (shown as circle) attached to the first DNA double strand is not identical to the second fluorescent dye (shown as star) attached to the second DNA double strand.

On the left part the competitor compound binds to a binding site within the protein, leading to an interlinking between the two DNA double strands. The interlinking brings the fluorescent dyes into proximity with the solid surface and the solid surface quenches the fluorescence emitted by the fluorescence dyes which are therefore shown as black circle and black star. When the solid surface is contacted with the small molecule, the interlinking by the competitor compound is disrupted and the distance between the fluorescent dye and the solid surface increases, leading to an increase in fluorescence (indicated by rays surrounding the circle and the star), see right part.

d) This figure shows the association (left) and dissociation (right) of the small molecule ATP from the protein PKA using the competitor compound adenine and a Rhodamine fluorescent dye using a first and a second DNA double strand. In this case, the competitor compound does not have significant quenching activity so that the quenching is effected by the metal surface. The fluorescence increases upon binding of the small molecule, since the interlinking between the first and the second DNA double strand is disrupted.

e) This figure shows the association (left) and dissociation (right) of the small molecule desthiobiotin from the protein streptavidin using the competitor compound desthiobiotin and a rhodamine fluorescent dye using a first and a second DNA double strand. Due to the binding of the desthiobiotin to the DNA linker it has a lower affinity to streptavidin than the free desthiobiotin. In this case, the release of the competitor compound leads to a strong increase of fluorescence which indicates that the increase is not only due to a disruption of the interlinking, but also to a fluorescence enhancing effect.

FIG. 3: Intramolecular interaction between competitor compound (shown as hexagon) and protein (shown as circle with an opening) wherein the protein, the competitor compound and the fluorescent dye (shown as circle surrounded by rays) are all attached to the same branched DNA double strand.

a) On the left part the competitor compound which is attached to a first branch of the branched DNA double strand binds to a binding site within the protein which is attached to a second branch of the same branched DNA double strand. By this binding the distance between competitor compound and the fluorescent dye is increased and the quenching effect of the competitor compound is reduced. When the solid surface is contacted with the small molecule, the competitor compound is released and interacts with the fluorescent dye, leading to quenching and consequently a decrease in the fluorescence.

b) This figure shows the association (left) and dissociation (right) of the small molecule staurosporine from the protein PKA using the competitor compound VI16832 and a Rhodamine fluorescent dye using a branched DNA double strand. The fluorescence decreases upon binding of the small molecule due to the quenching by the competitor compound.

c) This figure shows the association (left) and dissociation (right) of the small molecule dasatinib from the protein ABL kinase using the competitor compound VI16832 and a Rhodamine fluorescent dye using a branched DNA double strand. The fluorescence decreases upon binding of the small molecule due to the quenching by the competitor compound.

d) This figure shows the association (left) and dissociation (right) of the small molecule compound 18 from the protein PKA using the competitor compound VI16832 and a Rhodamine fluorescent dye using a branched DNA double strand. The fluorescence decreases upon binding of the small molecule due to the quenching by the competitor compound.

e) This figure shows the association (left) and dissociation (right) of the small molecule sorafenib from the protein ABL kinase using the competitor compound VI16832 and a Rhodamine fluorescent dye using a branched DNA double strand. The fluorescence decreases upon binding of the small molecule due to the quenching by the competitor compound.

FIG. 4: Intermolecular interaction between competitor compound (shown as hexagon) and protein (shown as circle with an opening) wherein the protein, the competitor compound and the fluorescent dye (shown as circle surrounded by rays) are attached to a branched DNA double strand.

a) On the left part the competitor compound which is attached to a first branched DNA double strand binds to a binding site within the protein which is attached to a second branched DNA double strand, leading to an interlinking between the two branched DNA double strands. The interlinking brings the fluorescent dyes bound to both the first and the second branched DNA double strand into proximity with the solid surface and the solid surface quenches the fluorescence emitted by the fluorescence dyes which are therefore shown as black circles. When the solid surface is contacted with the small molecule, the interlinking between the branched DNA double strands is interrupted and the distance between the fluorescent dye and the solid surface increases, leading to an increase in fluorescence (indicated by rays surrounding the circle), see right part.

b) On the left part the competitor compound which is attached to a first branched DNA double strand binds to a binding site within the protein which is attached to a second branched DNA double strand and the fluorescent dye which is attached to the first branched DNA double strand emits fluorescence. When the solid surface is contacted with the small molecule, the competitor compound is released, leading to quenching of the fluorescence emitted by the fluorescent dye which is therefore shown as a black circle (see right part).

c) On the left part the competitor compound which is attached to a first branched DNA double strand binds to a binding site within the protein which is attached to a second branched DNA double strand. By this binding an inherent quencher (shown as square) which is also attached to the first branched DNA double strand quenches the fluorescence emitted by the fluorescent dye (shown as black circle) which is attached to the second branched DNA double strand. When the solid surface is contacted with the small molecule, the competitor compound is released, thereby separating the inherent quencher and the fluorescent dye which leads to an increase in fluorescence, indicated by rays surrounding the circle (see right part).

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments and with reference to certain figures, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±20%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)" etc. relate to steps of a method or use or assay there is no time or time interval coherence between the steps unless indicated otherwise, i.e. the steps may be carried out simultaneously or there may be time intervals of seconds, minutes, hours, days, weeks, months or even years between such steps, unless otherwise indicated in the application as set forth herein above or below.

Technical terms are used by their common sense. If a specific meaning is conveyed to certain terms, definitions of terms will be given in the following in the context of which the terms are used.

The method of the present invention is used to detect and/or analyze the interaction between a protein and a small molecule.

The term "interaction" particularly refers to the binding of the small molecule to the protein.

The term "detecting" means that it can be determined whether such an interaction indeed exists or not.

The characterization of a known interaction includes the determination of the binding kinetics, i.e. the kinetics of association and dissociation between the protein and the small molecule.

The protein used in the method of the present invention may be any protein which is capable of interacting with a small molecule. Examples of proteins which are capable of interacting with small molecules include, but are not limited to, enzymes, intracellular or cell surface receptors, ligand transport proteins and transmembrane proteins.

Preferably, the protein is an enzyme. Enzymes are proteins which catalyze chemical reactions. The enzymes can be classified into the following categories: oxidoreductases, transferases, hydrolases, lyases, isomerases and ligases.

Oxidoreductases are enzymes that catalyze the transfer of electrons from one molecule, the reductant, also called the electron donor, to another, the oxidant, also called the electron acceptor. Examples of oxidoreductases include alcohol dehydrogenases, dihydrofolate reductase and nitrogenase.

Transferases transfer a functional group from a donor molecule to an acceptor molecule. Examples of transferases include acyl tranferases, glycosyl transferases, phosphorus transferases and sulfur transferases.

Hydrolases catalyze the hydrolysis of a chemical bond. Examples of hydrolases include proteases, phosphodiesterases and lipases.

Lyases catalyze the breaking of chemical bonds by a reaction other than hydrolysis. Examples of lyases include dehydratases, decarboxylases and cyclases.

Isomerases are enzymes which convert a molecule from one isomer to another. Isomerases can further subdivided into racemases, epimerases, cis-trans isomerases, intramolecular oxidoreductases, intramolecular transferases and intramolecular lyases.

Ligases are enzymes which catalyze the joining of two large molecules by forming a new bond. One example of a ligase is a DNA ligase.

Preferably, the enzyme is a kinase, i.e. a transferase which transfers phosphate groups from a donor to a substrate. The kinases can be further classified into protein kinases, lipid kinases and carbohydrate kinases, depending on the substrate to which the phosphate group is transferred. More preferably, the kinase is a protein kinase which transfers a phosphate group to a protein. Examples of protein kinases include protein kinase A (PKA), protein kinase B (PKB), protein kinase C (PKC), tyrosine kinases such as ABL-1, receptor tyrosine kinases, cyclin-dependent kinase and mitogen-activated protein kinases such as RAF, MEK and ERK.

The term "small molecule" is intended to include organic molecules with a molecular weight of 100 Dalton to 8,000 Dalton. Preferably, the small molecule has a molecular weight of 200 to 1,000 Dalton. In particular, the small molecule may be a small chemical fragment. The term "small molecule" is not intended to include fluorescent dyes. Further, the term "small molecule" is not intended to include nucleic acid polymers, large proteins and polysaccharides. However, the building blocks of nucleic acid polymers, large proteins and polysaccharides, i.e. nucleotides, amino acids and monosaccharides, and small oligomers thereof can be considered as small molecules. In particular, the term "small molecule" is intended to include peptides with a size of 250 to 8,000 Dalton.

The term "solid surface" is to be understood in its broadest sense as a structure to which a linker can be coupled reversibly or irreversibly and includes, for example, planar matrices such as chips or beads. The solid surface may be made of any substance to which a linker can be attached and includes glass, a degenerate semiconductor and a metal. Preferably, the solid surface is a metal surface. Suitable metal surfaces include gold, silver, platinum or titanium surfaces. More preferably, the metal surface is a gold surface. For the methods described herein, a biochip may be used which comprises a film on top of a substrate. For example, a gold film of 5-300 nm thickness may be used on a glass substrate. In one embodiment, the gold film may function as a quenching layer. Due to the coupling of the protein, the fluorescent dye and the competitor compound to the solid surface via the linker, these components are not in solution, but have a defined spatial relationship to each other. Further, the use of a solid surface allows the rapid exchange of solutions which are contacted with the solid surface and the molecules bound thereto.

Within the method of the present invention a "linker" is a linear or branched molecule which is bound to the solid surface with one end and to which at least one of the protein, the at least one fluorescent dye and the competitor compound is bound on the other end. A linker is considered as "branched", if the linker molecule itself is branched, independent of the molecules attached to it. The linker may be any molecule which does not significantly interfere with the binding of the competitor compound or the small molecule to the protein. Additionally, the linker may be any molecule which does not significantly interfere with the fluorescence emitted by the fluorescent dye. Suitable linkers are known to the skilled person and include a linear or branched nucleic acid linker, a linear or branched oligosaccharide linker, a dextran linker, a polyethylene glycol linker, a peptide linker and a linear or branched alkyl chain linker. The linker may have a length of 1 to 100 nm, preferably of 5 to 70 nm, more preferably of 10 to 60 nm and most preferably of 15 to 40 nm. Preferably, the linker is a nucleic acid linker. The nucleic acid linker may have a length of three to 300 nucleotides, preferably of 15 to 210 nucleotides, more preferably of 30 to 180 nucleotides and most preferably of 45 to 120 nucleotides.

The term "nucleic acid" refers to any type of nucleic acid molecule such as DNA or RNA or PNA or LNA with DNA being the preferred nucleic acid.

The nucleic acid linker is preferably at least partially double-stranded, i.e. at least 50%, preferably at least 60%, more preferably at least 70% and most preferably at least 80% of the nucleotides are hybridized to a complementary nucleotide. If a linear nucleic acid linker is used, the nucleic acid linker is preferably double-stranded over its complete length, meaning that all nucleotides of a first single-stranded nucleic acid molecule are hybridized to the complementary nucleotide in the second single-stranded nucleic acid molecule. If a branched nucleic acid linker is used, the linker is preferably double-stranded to the largest extent, meaning that only the branching point comprises one or more nucleotides which do not hybridize to another nucleotide in a complementary strand. The double-stranded portion remains intact when the method of the present invention is performed. The binding of the small molecule or the competitor compound to the protein does not lead to a disruption of the double strand.

The double-stranded nucleic acid linker may consist of DNA, RNA, PNA and LNA homoduplexes and heteroduplexes thereof such as DNA/RNA, DNA/PNA, DNA/LNA, RNA/PNA and PNA/LNA. The kind of nucleic acid used to form the linker may influence the stability of the double strand so that the minimal length required for the formation of a stable double strand depends on the type of nucleic acid forming the double strand.

Within the meaning of the present invention a "nucleic acid structure" is a secondary structure formed by the interaction between four different single-stranded nucleic acid molecules, leading to a branched nucleic acid molecule to which the protein, the fluorescent dye, the competitor compound and possibly the quencher are attached. An example of such a nucleic acid structure is shown in FIG. 4.

A "fluorescent dye" is a fluorescent chemical compound which absorbs light of a specific wavelength and re-emits the light at a longer wavelength. Fluorescent dyes typically contain several combined aromatic groups, or planar or cyclic molecules with several π bonds. Suitable fluorescent dyes are known to the skilled person and include FITC, fluoresceine, rhodamine and derivatives thereof, such as rhodamine green and rhodamine red, cyanine, cyanine5, phycoerythrine, BODIPY-FL, Alexa Fluor dyes, Atto dyes available from ATTO-TEC, DyLight fluorescent dyes and allophycocyanin (APC) and conjugates thereof.

For binding the linker to a solid surface, the linker may comprise a chemical group which facilitates the attachment to the surface via a chemical reaction. Suitable chemical groups are known to the skilled person and depend on the surface to which the linker is to be attached. If the substrate is a gold surface, the chemical group is preferably a thiol group such as $(CH_2)_6$—SH or di-thiol phosphoramidite. According to another exemplary embodiment of the invention the chemical group may be chosen from the group that contains one of—or a combination of—the following reactive groups: aldehyde, ketone, thiol, amine, carboxyl, hydrazine, hydrazide, hydroxyl, glycan, azide, alkyne, alkene, silicon, and any combination thereof. For glass or silicium surfaces a silane group may be used. If the surface is modified with avidin, the chemical group may be biotin. An overview of further chemical groups useful for attaching linkers to a solid surface is provided on the website of the company Integrated DNA Technologies (IDT). Methods for attaching a chemical group to a nucleic acid molecule are well-known and include the use of thiolated nucleotides (see Hegner et al. (1993) FEBS 336(3): 452-456). Nucleic acid molecules with an attached linker can be obtained commercially from companies such as Biomers, Ella Biotech and IDT.

In the present invention the competitor compound is preferably covalently bound to the linker. The exact method for binding the competitor compound to the linker depends on the chemical structure of the competitor compound. Reactive groups of the competitor compound which can be used for binding include aldehyde, thiol, amine, carboxyl, hydrazine, hydrazide, hydroxyl, azide and alkyne groups. Between the linker and the competitor compound additional moieties different from both the linker and the competitor compound may be present. For example, if the linker is a nucleic acid linker, a short alkyl chain or one or more ethylene oxides may be present between the nucleic acid linker and the competitor compound.

Within the method of the present invention the protein can be bound to the linker by covalent binding. The person skilled in the art is aware of methods for covalently attaching compounds such as proteins to linkers such as nucleic acid molecules. One possibility is to modify the nucleic acid molecule by 6-maleimidohexanoic acid N-hydroxysuccinimide ester and then to react the modified DNA with the protein having suitable amino acid residues for conjugation (see, e.g., Fujiwara et al. (1988). J. Immunol. Methods 112: 77-83; Peeters et al. (1989) J. Immunol. Methods 120: 133-143; Stephanopoulus et al. (2011) Nat. Chem. Biol. 7: 876-884). Further, kits are available for producing protein-nucleic acid conjugates, for example from Dynamic Bio sensors. An overview of different conjugation techniques is provided in Hermanson, Bioconjugate Techniques, Elsevier, third edition 2013 and in Mark, Bioconjugation Protocols, Humana Press, second edition 2011.

Alternatively, the protein can be bound to the linker via a non-covalent interaction. For example, the protein may comprise a tag such as a His tag, a HA tag, a FLAG tag, a Strep tag, a myc tag, a VSV tag or a GST tag which interacts with the corresponding binding partner which is attached to the linker.

Within the present invention the term "competitor compound" is a molecule which is able to bind reversibly to the binding site of the protein which is used in the method. In one embodiment, the competitor compound is not an antibody or a peptide having a size of more than five amino acids. In one embodiment, the competitor compound binds to the active site of an enzyme. In another embodiment, the competitor compound binds to an allosteric site of an enzyme. If the compound which naturally binds to the protein is known, the competitor compound may be selected to have a structure which is similar to that of the compound naturally binding to the protein. The size of the competitor compound is similar to that of the small molecule provided above. For example, the size is between 100 and 2,000 Daltons, preferably between 200 and 1,000 Daltons. In one embodiment, the competitor compound has a lower affinity to the protein used in the method of the present invention than the small molecule. In one embodiment, the competitor compound is different from the small molecule. This means that the structure of the competitor compound is not identical to the structure of the small molecule. The competitor compound can be selected such that it binds to substantially all proteins of the protein class to which the protein used in the method of the present invention belongs. Alternatively, the competitor compound may be selected such that it binds only to some of the proteins of the protein class to which the protein used in the method of the present invention belongs, for example to a specific subclass. In another alternative, the competitor compound may be selected such that it binds specifically only to the protein used in the method of the present invention. If necessary, it can be confirmed by binding assays that the competitor compound is able to bind to the protein used in the method, before the method of the present invention is performed.

If the protein used in the method of the present invention is a kinase, the competitor compound may be a broad spectrum kinase inhibitor. Such broad spectrum kinase inhibitors are known to the skilled person and include, but are not limited to, VI16832, CTX-0294885, apigenin, H7-dihydrochloride, H9-dihydrochloride, hypericin, Indirubin-3'-oxime, 5-Iodotubercidin, K252a, PKC 412, Ro 31-8220 mesylate, sorafenib, staurosporine and CZC8004.

Kinase inhibitors which bind only to kinases of one or more specific subclasses, but not to all kinases, include imatinib, gefitinib, sunitinib, dasatinib, pelitinib, lapatinib, RO 320-1195, vandetanib, purvalanol and PD173955.

In the absence of the small molecule the competitor compound binds to the protein due to its affinity to the protein. If the small molecule is added to the solid surface, it will replace the competitor compound on the protein, leading to the release of the competitor compound. The release of the competitor compound has an effect on the fluorescence emitted by the fluorescent dye which therefore changes. This change in fluorescence can be monitored in real time, allowing a very precise characterization of the interaction between the protein and the small molecule.

Suitable conditions which allow the small molecule to replace the competitor compound involve the use of a suitable buffer such as a buffer comprising sodium chloride and a buffer, such as a buffer comprising sodium chloride and a phosphate buffer (PBS). The selection of the buffer system for replacing the competitor compound is not critical for the method of the present invention. The buffer may contain reducing agents (e.g thiol-based agents or TCEP) and mono- or divalent ions.

The change in fluorescence which is effected by the release of the competitor compound can both be an increase and a decrease, depending on the experimental setup used.

In a first embodiment, the competitor compound interacts with the fluorescent dye and this interaction leads to a quenching of the fluorescence of the fluorescent dye. In this case, the fluorescence decreases when the competitor compound is released from the protein, since then it can interact with the fluorescent dye.

In a second embodiment, the competitor compound has no quenching effect on the fluorescent dye. In this case, quenching can be effected by binding a dark quencher to the linker to which the protein is bound. A "dark quencher" is a substance that absorbs excitation energy from a fluorescent dye and dissipates the energy as heat. Examples of dark quenchers include black hole quenchers (e.g. BHQ1, BHQ2), IR-Dye QC-1 and Qx1 quenchers which are able to absorb fluorescence from the whole visible spectrum. In this case, the fluorescence increases when the competitor compound is released from the protein, since then the dark quencher and the fluorescent dye are spatially separated.

In a third embodiment, the fluorescence may be quenched by the solid surface, if the solid surface is a metal surface or a degenerate semiconductor. In this case, the interaction of the competitor compound and the protein reduces the distance of the fluorescent dye to the solid surface, leading to a decrease of the fluorescence. If the small molecule releases the competitor compound, the distance between the fluorescent dye and the solid surface increases, leading to an increase in the fluorescence.

The term "quenching" as used herein refers to any process which decreases the fluorescence intensity of the fluorescent dye.

The association of the small molecule with the protein is equivalent to the binding of the small molecule to the protein and the dissociation of the small molecule from the protein is equivalent to the release of the small molecule from the protein. The present invention allows to measure the time course of association and/or dissociation by continuously detecting the change in fluorecence after the solid surface has been contacted with the small molecule. The term "continuously detecting" means that the fluorescence is measured without any break until the fluorescence does not change any more, but remains at a stable value. This is in contrast to methods where a measurement is made only at the beginning and at the end of a process.

In the following, some particular embodiments of the method of the present invention are discussed. These embodiments are discussed with reference to a nucleic acid linker such as the one used in the examples of the present application. However, the person skilled in the art knows that the nucleic acid linker can be replaced by other linkers which are disclosed herein.

In a first embodiment, the present invention is directed to a method for detecting and/or characterizing the interaction between a protein and a small molecule, comprising the steps of:

a) providing a solid surface, preferably a gold surface, to which one double-stranded nucleic acid linker is bound, wherein the protein, a fluorescent dye and a competitor compound are attached to the nucleic acid linker and wherein the competitor compound binds to the protein;

b) contacting the solid surface with the small molecule under conditions that allow the small molecule to bind to the protein and to release the competitor compound from the protein; and c) detecting a change in the fluoresence emitted by the fluorescent dye.

In this first embodiment, the release of the competitor compound may either enhance the fluorescence emitted by the fluorescent dye, leading to an increase of the fluorescence emitted by the fluorescent dye, or it may quench the fluorescence emitted by the fluorescent dye, leading to a decrease of the fluorescence emitted by the fluorescent dye.

This embodiment is shown in FIG. 1.

In a second embodiment, the present invention is directed to a method for detecting and/or characterizing the interaction between a protein and a small molecule, comprising the steps of:

a) providing a solid surface, preferably a gold surface, to which a first and a second double-stranded nucleic acid linker is bound, wherein the protein is attached to the first double-stranded nucleic acid linker and a fluorescent dye and a competitor compound are attached to the second double-stranded nucleic acid linker and wherein the competitor compound binds to the protein;

b) contacting the solid surface with the small molecule under conditions that allow the small molecule to bind to the protein and to release the competitor compound from the protein; and c) detecting a change in the fluorescence emitted by the fluorescent dye.

In this second embodiment, the binding of the competitor compound to the protein reduces the quenching of the competitor compound so that the fluorescent dye emits fluorescence as long as the competitor compound binds to the protein. When the small molecule releases the competitor compound, the competitor compound interacts with the fluorescent dye and quenches the fluorescence emitted by the fluorescent dye, thereby leading to a decrease in fluorescence emitted by the fluorescent dye. In some cases, the binding of the competitor compound to the protein reduces the fluorescence emitted by the fluorescent dye. When the small molecule releases the competitor compound, the competitor compound interacts with the fluorescent dye and increases the fluorescence emitted by the fluorescent dye.

Alternatively, if the competitor compound is not able to quench the fluorescence emitted by the fluorescent dye, the change in fluorescence may be detected by the quenching activity of the solid surface. In this case, the solid surface is a metal surface, preferably a gold surface, which has quenching activity. The binding of the competitor compound to the protein leads to a connection of the first and the second nucleic acid linkers so that the distance between the fluorescent dye and the solid surface is decreased and the fluorescence emitted by the fluorescent dye decreases. When the small molecule releases the competitor compound, the connection between the first and the second nucleic acid linkers is disrupted and the distance between the fluorescent dye and the solid surface increases, leading to an increase in fluorescence.

The sequences of the single strands which hybridize to form the nucleic acid linkers may be the same for both the first and the second double-stranded nucleic acid linker. Alternatively, the sequences of the single strands forming the first double-stranded nucleic acid linker may be different from the sequences of the single strands forming the second double-stranded nucleic acid linker. Preferably, the sequences of the single strands forming the first double-stranded nucleic acid linker are different from the sequences of the single strands forming the second double-stranded nucleic acid linker.

In a third embodiment, the present invention is directed to a method for detecting and/or characterizing the interaction between a protein and a small molecule, comprising the steps of:

a) providing a solid surface, preferably a gold surface, to which a first and a second double-stranded nucleic acid linker is bound, wherein the protein and a first fluorescent dye are attached to the first double-stranded nucleic acid linker and a second fluorescent dye and a competitor compound are attached to the second double-stranded nucleic acid linker and wherein the competitor compound binds to the protein;

b) contacting the solid surface with the small molecule under conditions that allow the small molecule to bind to the protein and to release the competitor compound from the protein; and c) detecting a change in the fluoresence emitted by the fluorescent dye.

Figure 2A:
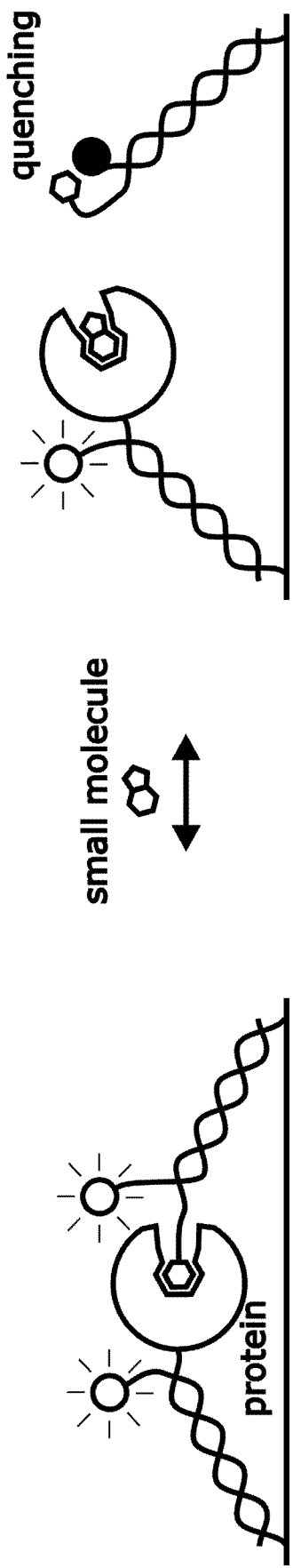

In this third embodiment, the binding of the competitor compound to the protein reduces the quenching of the competitor compound so that the fluorescent dye attached to the second double-stranded nucleic acid molecule emits fluorescence as long as the competitor compound binds to the protein. When the small molecule releases the competitor compound, the competitor compound interacts with the second fluorescent dye and quenches the fluorescence emitted by the second fluorescent dye, thereby leading to a decrease in fluorescence emitted by the second fluorescent dye. This embodiment is shown in FIG. 2a.

In some cases, the binding of the competitor compound to the protein reduces the fluorescence emitted by the fluorescent dye. When the small molecule releases the competitor compound, the competitor compound interacts with the fluorescent dye and increases the fluorescence emitted by the fluorescent dye.

Figure 2B:
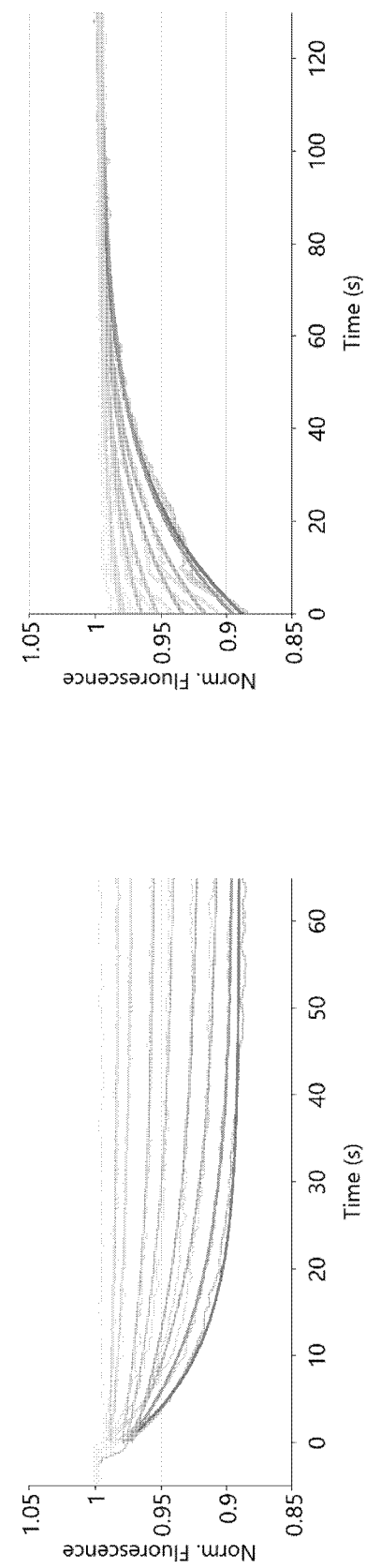
Figure 2C:
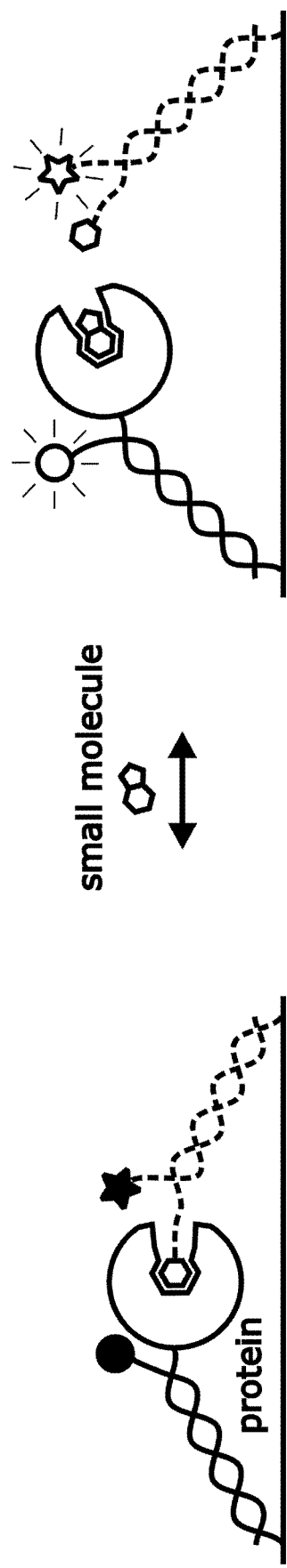

Alternatively, if the competitor compound is not able to quench the fluorescence emitted by the fluorescent dye, the change in fluorescence may be detected by the quenching activity of the solid surface. In this case, the solid surface is a metal surface, preferably a gold surface, which has quenching activity. The binding of the competitor compound to the protein leads to a connection of the first and the second nucleic acid linkers so that the distance between the fluorescent dye and the solid surface is decreased and the fluorescence emitted by the fluorescent dye decreases. When the small molecule releases the competitor compound, the connection between the first and the second nucleic acid linkers is disrupted and the distance between the fluorescent dye and the solid surface increases, leading to an increase in fluorescence. This embodiment is shown in FIG. 2c.

The first and the second fluorescent dye may be the same or may be different.

The sequences of the single strands which hybridize to form the nucleic acid linkers may be the same for both the first and the second double-stranded nucleic acid linker. Alternatively, the sequences of the single strands forming the first double-stranded nucleic acid linker may be different from the sequences of the single strands forming the second double-stranded nucleic acid linker. If the first and the second fluorescent dye are different, the sequences of the single strands forming the first double-stranded nucleic acid linker are different from the sequences of the single strands forming the second double-stranded nucleic acid linker.

In a fourth embodiment, the present invention is directed to a method for detecting and/or characterizing the interaction between a protein and a small molecule, comprising the steps of:

a) providing a solid surface, preferably a gold surface, to which a branched nucleic acid linker is bound which comprises the following elements:

(i) a first and a second nucleic acid molecule which form a double strand with each other over a part of the first and a part of the second nucleic acid molecule;

(ii) a third nucleic acid molecule which forms a double strand with a part of the first nucleic acid molecule which does not form a double strand with the second nucleic acid molecule; and (iii) a fourth nucleic acid molecule which forms a double strand with a part of the second nucleic acid molecule which does not form a double strand with the first nucleic acid molecule, wherein:

a first fluorescent dye is attached to the second nucleic acid molecule;

a protein is attached to the third nucleic acid molecule, and a competitor compound is attached to the fourth nucleic acid molecule, and wherein the competitor compound binds to the protein;

b) contacting the solid surface with the small molecule under conditions that allow the small molecule to bind to the protein and to release the competitor compound from the protein; and c) detecting a change in the fluoresence emitted by the fluorescent dye.

In this fourth embodiment, the binding of the competitor compound to the protein reduces the quenching of the competitor compound so that the first fluorescent dye attached to the second double-stranded nucleic acid molecule emits fluorescence as long as the competitor compound binds to the protein. When the small molecule releases the competitor compound, the competitor compound interacts with the first fluorescent dye and quenches the fluorescence emitted by the first fluorescent dye, thereby leading to a decrease in fluorescence emitted by the first fluorescent dye. This embodiment is shown in FIG. 3.

Additionally, a second fluorescent dye may be attached to the first nucleic acid molecule.

This embodiment has the additional advantage that it is independent of the density with which the nucleic acid linker is immobilized to the solid surface, as the protein and the competitor compound are always close to each other. Additionally, this embodiment enables to obtain a high local concentration of the analytes.

In a fifth embodiment, the present invention is directed to a method for detecting and/or characterizing the interaction between a protein and a small molecule, comprising the steps of:

a) providing a solid surface, preferably a gold surface, to which at least a first and a second branched nucleic acid linker is bound each of which comprises the following elements:

(i) a first and a second nucleic acid molecule which form a double strand with each other over a part of the first and a part of the second nucleic acid molecule;

(iv) a third nucleic acid molecule which forms a double strand with a part of the first nucleic acid molecule which does not form a double strand with the second nucleic acid molecule; and (v) a fourth nucleic acid molecule which forms a double strand with a part of the second nucleic acid molecule which does not form a double strand with the first nucleic acid molecule, wherein:

a first fluorescent dye is attached to the second nucleic acid molecule;

a protein is attached to the third nucleic acid molecule, and a competitor compound is attached to the fourth nucleic acid molecule, and wherein the competitor compound attached to the first nucleic acid linker binds to the protein attached to the second nucleic acid linker;

b) contacting the solid surface with the small molecule under conditions that allow the small molecule to bind to the protein and to release the competitor compound from the protein; and c) detecting a change in the fluoresence emitted by the first fluorescent dye.

Figure 4A:
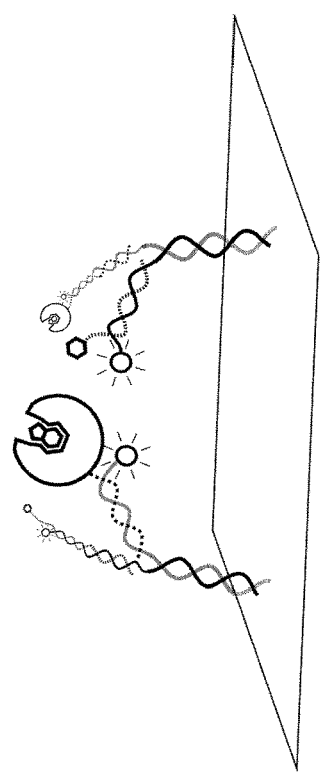
Figure 4A:
Figure 4A:
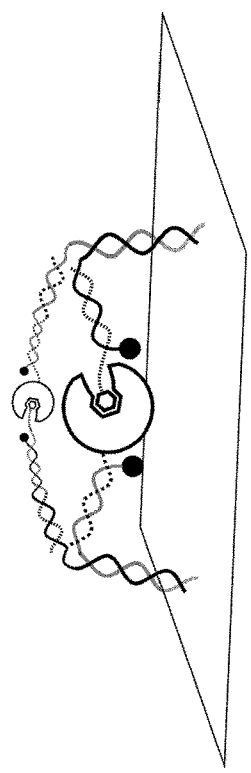
Figure 4B:
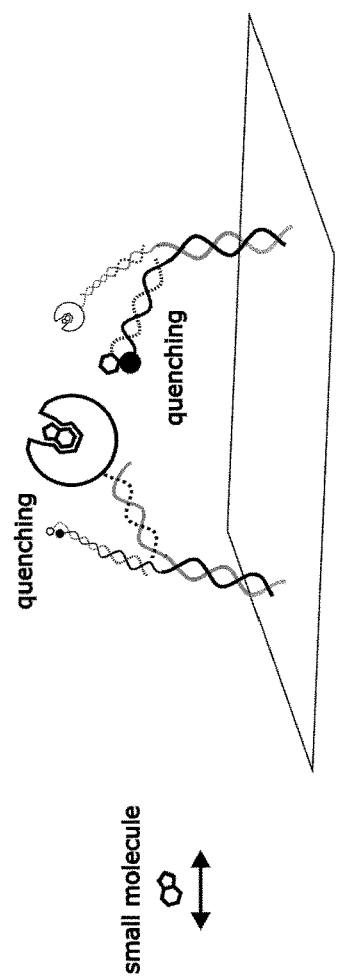
Figure 4B:
Figure 4B:
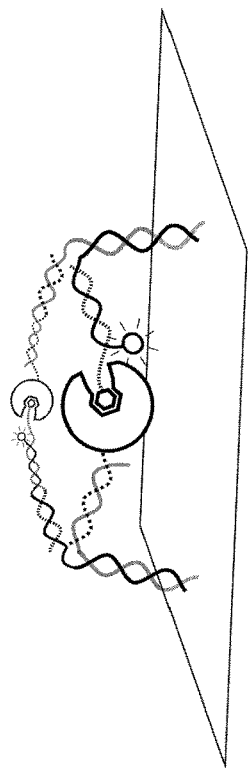

In this fifth embodiment, the binding of the competitor compound attached to the first nucleic acid linker to the protein attached to the second nucleic acid linker reduces the quenching of the competitor compound so that the fluorescent dye attached to the second double-stranded nucleic acid molecule emits fluorescence as long as the competitor compound binds to the protein. When the small molecule releases the competitor compound, the competitor compound interacts with the first fluorescent dye and quenches the fluorescence emitted by the first fluorescent dye, thereby leading to a decrease in fluorescence emitted by the first fluorescent dye. This embodiment is shown in FIG. 4b.

Additionally, a second fluorescent dye may be attached to the first nucleic acid molecule. The second fluorescent dye may be the same as the first fluorescent dye or it may be different from the first fluorescent dye.

Alternatively, if the competitor compound is not able to quench the fluorescence emitted by the first fluorescent dye, the change in fluorescence may be detected by the quenching activity of the solid surface. In this case, the solid surface is a metal surface, preferably a gold surface, which has quenching activity. The binding of the competitor compound to the protein leads to a connection of the first and the second branched nucleic acid linkers so that the distance between the fluorescent dye and the solid surface is decreased and the fluorescence emitted by the fluorescent dye decreases. When the small molecule releases the competitor compound, the connection between the first and the second branched nucleic acid linkers is disrupted and the distance between the fluorescent dye and the solid surface increases, leading to an increase in fluorescence. This embodiment is shown in FIG. 4a, wherein two identical fluorescent dyes are attached to the branched nucleic acid linker.

In a sixth embodiment, the present invention is directed to a method for detecting and/or characterizing the interaction between a protein and a small molecule, comprising the steps of:

a) providing a solid surface, preferably a gold surface, to which at least a first and a second branched nucleic acid linker is bound each of which comprises the following elements:

(i) a first and a second nucleic acid molecule which form a double strand with each other over a part of the first and a part of the second nucleic acid molecule;

(vi) a third nucleic acid molecule which forms a double strand with a part of the first nucleic acid molecule which does not form a double strand with the second nucleic acid molecule; and (vii) a fourth nucleic acid molecule which forms a double strand with a part of the second nucleic acid molecule which does not form a double strand with the first nucleic acid molecule, wherein:

a quencher is attached to the first nucleic acid molecule;
a fluorescent dye is attached to the second nucleic acid molecule;
a protein is attached to the third nucleic acid molecule, and
a competitor compound is attached to the fourth nucleic acid molecule, and wherein the competitor compound attached to the first nucleic acid linker binds to the protein attached to the second nucleic acid linker;

b) contacting the solid surface with the small molecule under conditions that allow the small molecule to bind to the protein and to release the competitor compound from the protein; and c) detecting a change in the fluoresence emitted by the fluorescent dye.

Figure 4C:
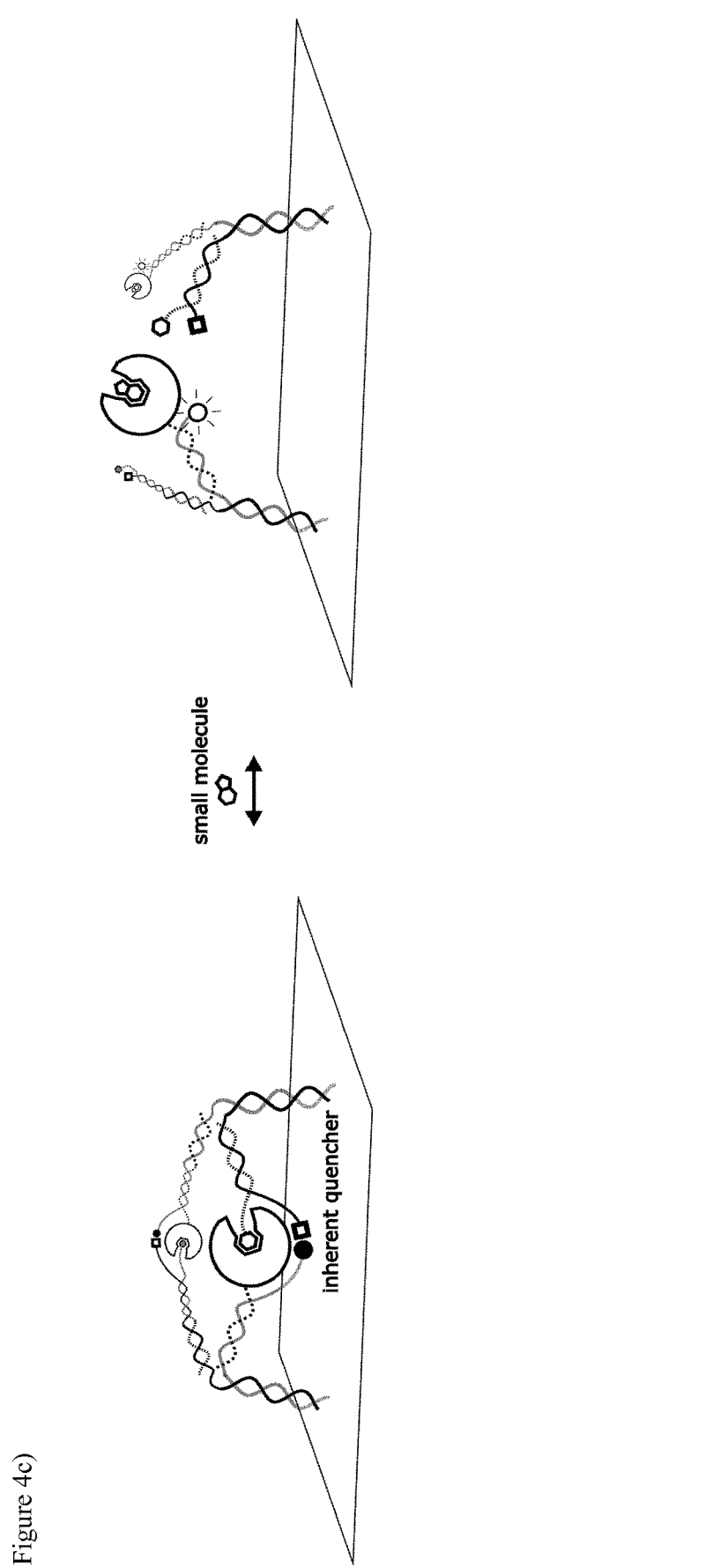

In this sixth embodiment, the binding of the competitor compound attached to the first branched nucleic acid linker to the protein attached to the second branched nucleic acid linker brings the quencher attached to the second branched nucleic acid linker into proximity of the fluorescent dye attached to the first branched nucleic acid linker, thereby quenching the fluorescence emitted by the fluorescent dye, leading to a decrease in the fluorescence emitted by the fluorescent dye as long as the competitor compound binds to the protein. When the small molecule releases the competitor compound, the distance between the quencher and the fluorescent dye increases, thereby leading to an increase in fluorescence emitted by the fluorescent dye. This embodiment is shown in FIG. 4c.

The following examples and figures are provided for illustrative purposes. It is thus understood that the examples and figures are not to be construed as limiting. The skilled person in the art will clearly be able to envisage further modifications of the principles laid out herein.

EXAMPLES

The following examples were obtained using a first and a second nucleic acid linker immobilized onto a chip surface, wherein the protein and a fluorescent dye are attached to the first nucleic acid linker and the competitor compound and a fluorescent dye are attached to the second nucleic acid linker. However, it is readily apparent to the skilled person that the method can also be performed using other linkers and linker configurations as described herein.

1. Protein Coupling to the DNA Linker

40 µg of thiol-modified DNA (linker) was incubated with 60 equivalents of hetero-bifunctional crosslinker (amine- and thiol-reactive) Sulfo-SMCC (Sigma-Aldrich) for 5 minutes in Phosphate buffered saline (PBS). The excess crosslinker was removed using two Zeba-desalting columns (Thermo Fisher Scientific) following the standard protocol. The activated DNA which was in the flowthrough from the columns was mixed with 100 µg of protein (i.e. cAMP-dependent proteinkinase A, p38 or streptavidin) and incubated for 1 h at 25° C. After amide bond formation between reactive lysines or the N-terminal alpha-amino group of proteins with NHS-ester on functionalized DNA, protein-DNA conjugates were purified in a one-step-purification using an anion-exchange column (FPLC system). The concentration of freshly prepared Protein-DNA conjugates was determined by absorbance measurement at a wavelength of 260 nm. The protein-DNA conjugates were diluted to a final concentration of 400 nM.

2. Competitor Compound Coupling to the DNA Linker a) By Amine Coupling

Competitor compound PP58 was coupled to the DNA linker via its primary amine group. To this end, 40 µg of thiol-modified DNA (linker) was incubated with 60 equivalents of hetero-bifunctional crosslinker (amine- and thiol-reactive) Sulfo-SMCC (Sigma-Aldrich) for 5 minutes in phosphate-buffered saline (PBS). The excess crosslinker was removed using two Zeba-desalting columns (Thermo Fisher Scientific) following the standard protocol. The activated DNA which was in the flowthrough from the columns was mixed with 100 µg of PP58 (Vichem) and incubated for 1 h at 25° C. in PBS with 1% DMSO. After amide bond formation between the primary amine group on PP58 with the NHS-ester on functionalized DNA, protein-DNA conjugates were purified in a one-step-purification using an C18 reverse phase column (HPLC system, Agilent), mobile phase: Mixture of $H_2O$/Acetonitrile, gradient from 5% to 80% Acetonitrile. The concentration of freshly prepared competitor compound-DNA conjugates was determined by absorbance measurement at a wavelength of 260 nm. The competitor compound-DNA conjugates were diluted to a final concentration of 400 nM. The above protocol is also applicable to other competitor compounds having an amine group such as adenine.

b) Preparation of the Adenine-DNA Conjugate

The conjugate between the competitor compound adenine and DNA was synthesized by Ella Biotech (Planegg, DE). Adenine was incorporated at the 5' end of the synthesized 48 mer DNA using a phosphoamidite chemistry and standard DNA synthesis protocols. Between the adenine and the DNA a stretch of three ethylene oxide molecules was introduced.

c) Preparation of the Desthiobiotin-DNA Conjugate

The conjugate between the competitor compound desthiobiotin and DNA was purchased from biomers (Ulm). Desthiobiotin was incorporated at the 5' end of the synthesized 48 mer DNA using a phosphoamidite chemistry and standard DNA synthesis protocols. Between the desthiobiotin and the DNA an alkyl stretch of six carbon atoms was introduced.

3. Chip Preparation

The biochip consists of a glass substrate (27×40 mm) with eight holes (1 mm diameter), which serve as in- and outlets for four flow channels. Au work electrodes (120 mm diameter) and Ito counter electrodes were arranged in four areas with six electrodes each and fabricated by standard optical lithography and metallization techniques. Before DNA immobilization, the surface was cleaned in freshly prepared Piranha solution (95% $H_2SO_4$:30% $H_2O_2$=2:1) for 15 min, followed by extensive rinsing with deionized water, 3 min sonication and drying with nitrogen.

5'-Thiolated 3'-Cy3 labelled single-stranded DNA was end-grafted to the gold electrodes via spotting with a picolitre dispensing system in immobilization buffer (10 mM Tris pH 7.4, 200 mM NaCl, 1 mM DNA). After 10 minutes incubation, the chip was assembled by using double adhesive film with die-cut flow channels as an intermediate layer and a cover slide as a top layer. The flow channels were 60 mm high and 1 mm wide, and covered one of the four electrode areas each. The DNA-modified Au electrodes were passivated and unspecifically bound DNA was removed by coadsorbing mercaptohexanol (1 mM in 'T'-buffer: 10 mM Tris pH 7.4, 50 mM NaCl) for 30 min (ref. 35).

4. Immobilization of the Protein- and Competitor Compound Coupled DNA

Biochips manufactured as described in section 3 carry double-stranded DNA on their surfaces. These surfaces were treated with a NaOH solution (pH 13) for 10 seconds to yield fully single-stranded DNA surfaces. For immobilization of competitor compound-DNA-conjugates and protein-DNA conjugates simultaneously, 25 µL of a 1:1 mixture of conjugates (final concentration: 200 nM each) in PBS were injected to the biochip surface. The immobilization is followed in real time, since a transition from ssDNA to dsDNA results in a gradual increase in fluorescence due to reduced distance dependent quenching of fluorescent dye and metallic chip surface. In the process of or prior to immobilization the competitor compound binds to the protein.

5. Fluorescence Measurement a) Measurement of Association and Dissociation of SB203580 with p38 Kinase The measurement of association of SB203580 with p38 kinase was recorded by injection of different concentrations (0, 10, 20, 40, 80, 160, 320, 640 nM) of SB203580 with a volume of 120 µL at flow rates of 100 µL/min in PBS including 1% DMSO onto a chip carrying PP58-DNA conjugates and p38-DNA conjugates prepared as described in examples 1 and 2. The measurement of SB203580 dissociation from the protein was recorded by injection of buffer without SB203580. Both measurements were made with the DRX device of Dynamic Biosensors which contains an epifluorescence microscope with photon counter. The result of this measurement is shown in FIG. 2b.

b) Measurement of Association and Dissociation of ATP with Protein Kinase A

Figure 2D:
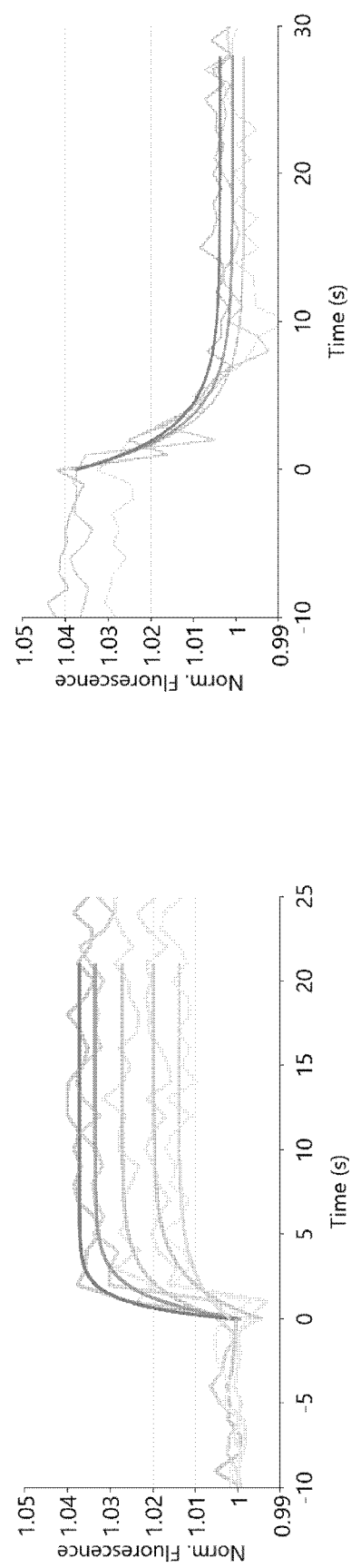
Figure 2E:
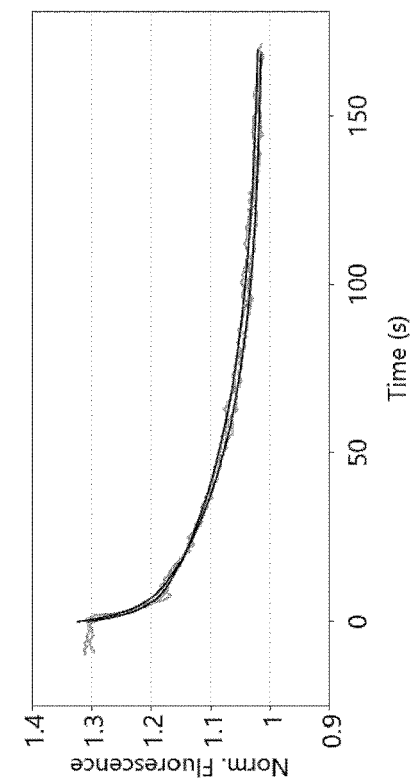
Figure 2E:
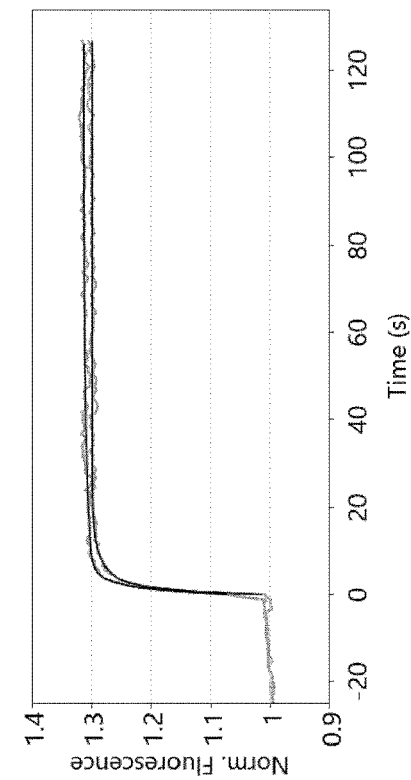

The measurement of association of ATP with protein kinase A was recorded by injection of different concentrations (62.5, 125, 250, 500 µM) of ATP with a volume of 120 µL at flow rates of 200 µL/min in TE40 buffer (10 mM Tris-HCl pH 7.4, 40 mM NaCl, 0.05% Tween 20, 50 µM EDTA/50 µM EGTA) including 2 mM $MgCl_2$ onto a chip carrying adenin-DNA conjugates and protein kinase A-DNA conjugates prepared as described in examples 1 and 2. The measurement of ATP dissociation from the protein was recorded by injection of buffer without ATP. Both measurements were made with the DRX device of Dynamic Biosensors which contains an epifluorescence microscope with photon counter. The result of this measurement is shown in FIG. 2d.

c) Measurement of Association and Dissociation of Desthiobiotin with Streptavidin The measurement of desthiobiotin association with streptavidin was recorded by injection of desthiobiotin with a concentration of 150 nM (two times) and a volume of 300 µL at flow rates of 100 µL/min in PBS including 1% DMSO onto a chip carrying desthiobiotin-DNA conjugates and streptavidin-DNA conjugates prepared as described in examples 1 and 2. The measurement of desthiobiotin dissociation from streptavidin was recorded by injection of buffer without desthiobiotin. Both measurements were made with the DRX device of Dynamic Biosensors which contains an epifluorescence microscope with photon counter. The result of this measurement is shown in FIG. 2e.

6. Fluorescence Measurement Using a Branched DNA Structure

Figure 3A:
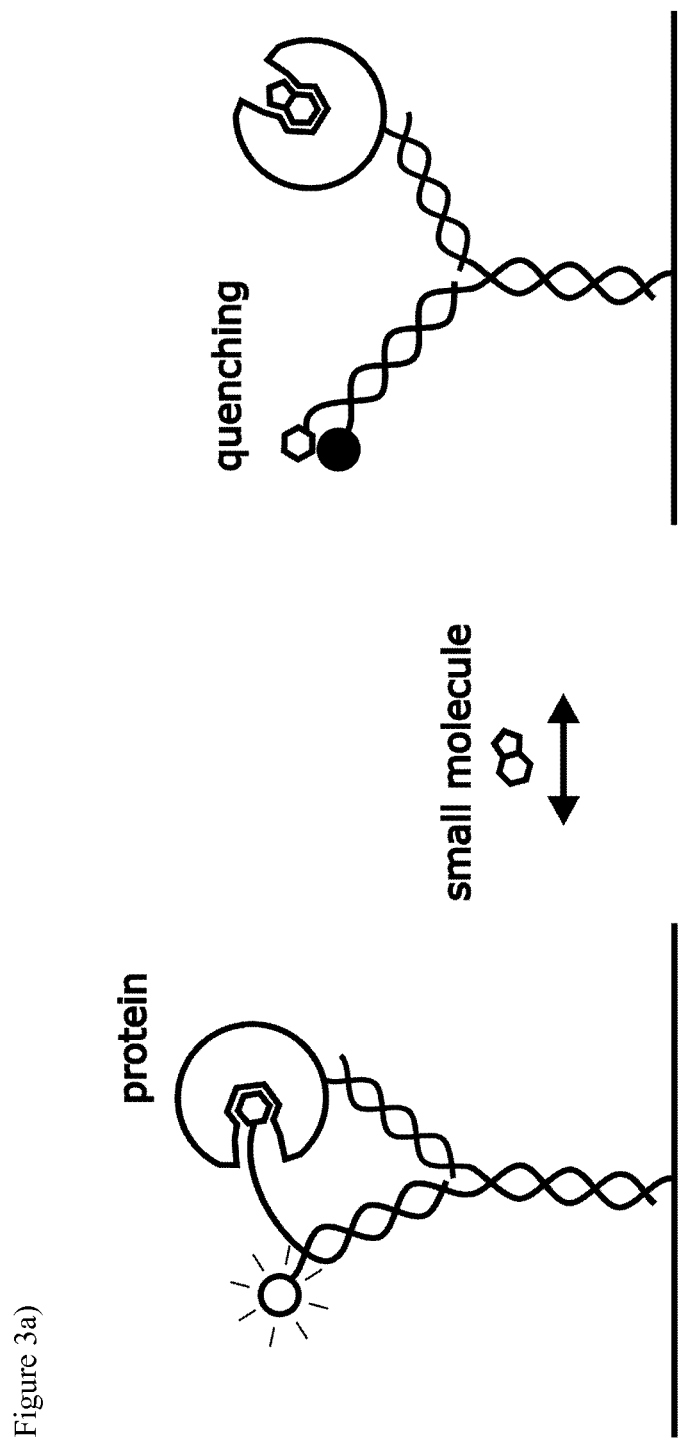
Figure 3B:
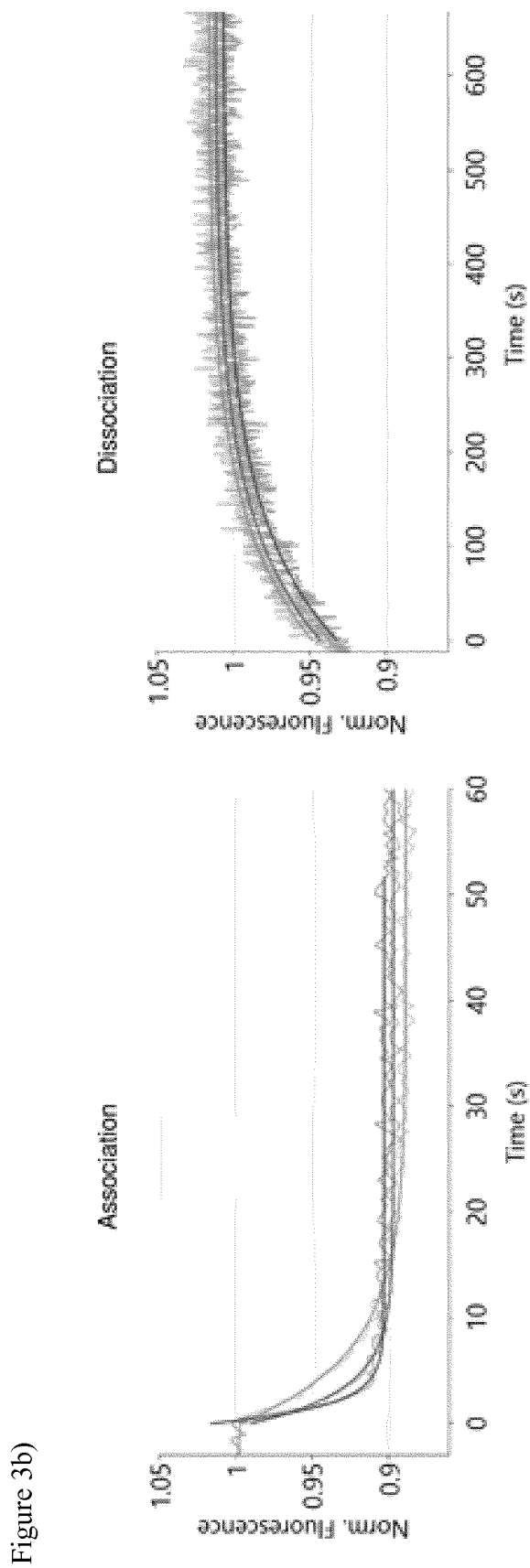
Figure 3C:
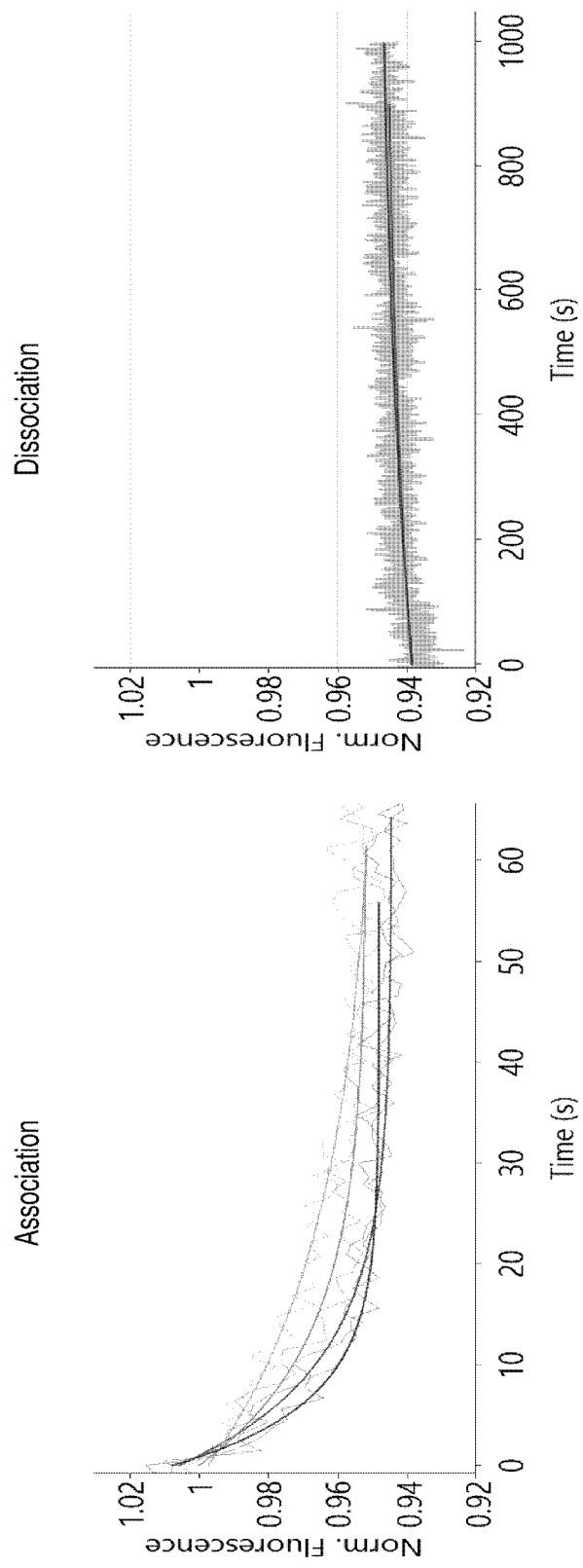
Figure 3D:
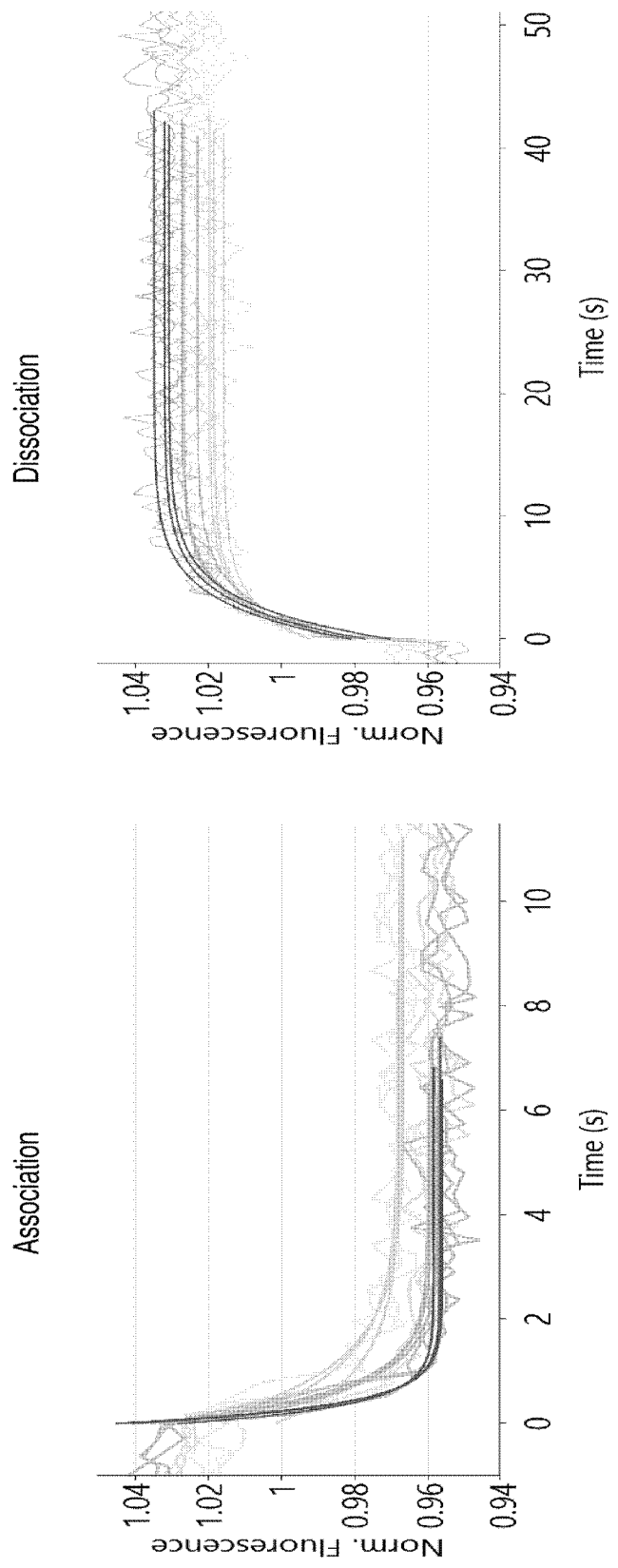

The proteins Protein kinase A and ABL kinase were coupled to the DNA as described in 1.) above and the competitor compound VI16832 was coupled to the DNA by amine coupling as described in 2a.) above. The fluorescence-labelled DNA was immobilized on the chip as described in 3.) above. The three other DNA molecules carrying the competitor compound, the protein and non-modified were hybridized to the immobilized DNA as described in 4.) above.

a) The measurement of association of staurosporine with protein kinase A was recorded by injection of different concentrations (25, 50, 100 nM) of staurosporine with a volume of 120 µL at flow rates of 100 µL/min in PBS including 1% DMSO onto a chip carrying a branched DNA structure to which VI16832 and protein kinase were coupled. The measurement of staurosporine dissociation from the protein was recorded by injection of buffer without staurosporine. Both measurements were made with the DRX device of Dynamic Biosensors which contains an epifluorescence microscope with photon counter. The result of this measurement is shown in FIG. 3b. The $K_D$ measured using this method is 1.2±0.1 nM which is in good agreement with the literature.

b) The measurement of association of dasatinib with ABL kinase was recorded by injection of different concentrations (10, 20, 25, 40 nM) of dasatinib with a volume of 120 µL at flow rates of 100 µL/min in PBS including 1% DMSO onto a chip carrying a branched DNA structure to which VI16832 and ABL kinase were coupled. The measurement of dasatinib dissociation from the protein was recorded by injection of buffer without dasatinib. Both measurements were made with the DRX device of Dynamic Biosensors which contains an epifluorescence microscope with photon counter. The result of this measurement is shown in FIG. 3c. The $K_D$ measured using this method is 376±32 pM which is in good agreement with the literature (Karaman et. al. (2008) Nat Biotechnol. 26(1): 127-132).

c) The measurement of association of compound 18 with protein kinase A was recorded by injection of different concentrations (2.5, 5, 10 µM) of compound 18 with a volume of 120 µL at flow rates of 100 µL/min in PBS including 1% DMSO onto a chip carrying branched DNA structure to which VI16832 and protein kinase A were coupled. The measurement of compound 18 dissociation from the protein was recorded by injection of buffer without compound 18. Both measurements were made with the DRX device of Dynamic Biosensors which contains an epifluorescence microscope with photon counter. The result of this measurement is shown in FIG. 3d. The $K_D$ measured using this method is 1.3±0.1 µM which is in good agreement with the literature (ITC measurements, Prof. G. Klebe, University of Marburg, Germany).

d) The measurement of association of sorafenib with ABL kinase was recorded by injection of different concentrations (0, 250, 500, 1000, 2000 nM) of sorafenib with a volume of 120 µL at flow rates of 100 µL/min in PBS including 1%

Figure 3E:
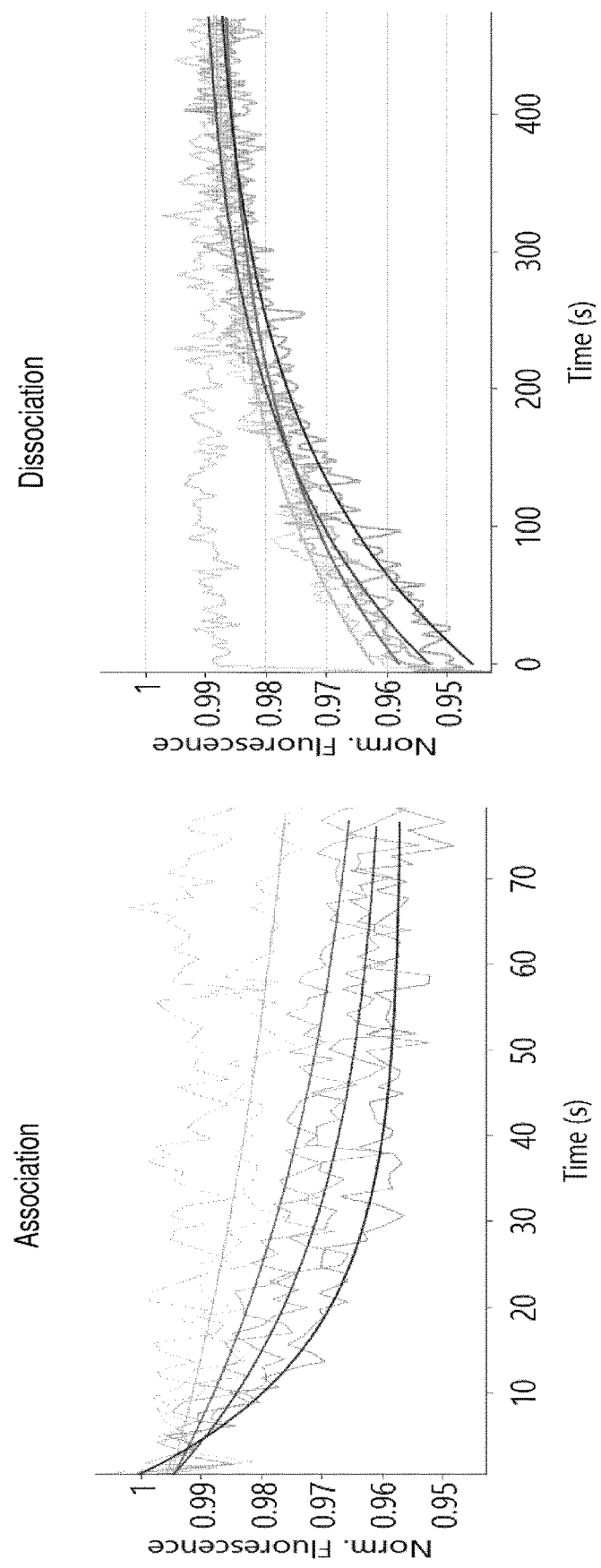

DMSO onto a chip carrying a branched DNA structure to which VI16832 and ABL kinase were coupled. The measurement of sorafenib dissociation from the protein was recorded by injection of buffer without sorafenib. Both measurements were made with the DRX device of Dynamic Biosensors which contains an epifluorescence microscope with photon counter. The result of this measurement is shown in FIG. 3e. The $K_D$ measured using this method is 196±17 nM which is in good agreement with the literature (Karaman et. al. (2008) Nat Biotechnol. 26(1): 127-132).

The invention claimed is:

1. A nucleic acid structure comprising:
   (i) a first and a second nucleic acid molecule which form a double strand with each other over a part of the first and a part of the second nucleic acid molecule;
   (ii) a third nucleic acid molecule which forms a double strand with a part of the first nucleic acid molecule which does not form a double strand with the second nucleic acid molecule; and
   (iii) a fourth nucleic acid molecule which forms a double strand with a part of the second nucleic acid molecule which does not form a double strand with the first nucleic acid molecule, wherein:
   a fluorescent dye is attached to the first nucleic acid molecule;
   a quencher is attached to the second nucleic acid molecule;
   a protein is attached to the third nucleic acid molecule, and
   a competitor compound is attached to the fourth nucleic acid molecule.

2. The nucleic acid structure of claim 1, wherein the nucleic acid structure is attached to a solid surface.

3. A method for characterizing the interaction between a protein and a molecule, comprising contacting the molecule with the nucleic acid structure of claim 1, wherein the competitor compound of the nucleic acid structure is bound to the protein, under conditions that allow the molecule to bind to the protein and to release the competitor compound from the protein, and detecting a change in the fluorescence emitted by the fluorescent dye.

* * * * *